(12) United States Patent
Seaton et al.

(10) Patent No.: US 6,572,256 B2
(45) Date of Patent: Jun. 3, 2003

(54) MULTI-COMPONENT, PRODUCT HANDLING AND DELIVERING SYSTEM

(75) Inventors: James P. Seaton, Chatham, NJ (US); Donald Barker, Sandy Hook, CT (US)

(73) Assignee: Immedica, Chatham, NJ (US)

( * ) Notice: Subject to any disclaimer, the term of this patent is extended or adjusted under 35 U.S.C. 154(b) by 0 days.

(21) Appl. No.: 10/266,053

(22) Filed: Oct. 7, 2002

(65) Prior Publication Data

US 2003/0067837 A1 Apr. 10, 2003

Related U.S. Application Data

(60) Provisional application No. 60/327,655, filed on Oct. 9, 2001.

(51) Int. Cl.[7] .............................................. B01F 13/06
(52) U.S. Cl. ..................... 366/139; 366/163.1; 206/222
(58) Field of Search ............................... 366/139, 163.1; 206/219, 222; 604/415, 416, 87, 88

(56) References Cited

U.S. PATENT DOCUMENTS

| | | | | | |
|---|---|---|---|---|---|
| 3,872,867 | A | * | 3/1975 | Killinger | 604/413 |
| 3,945,382 | A | * | 3/1976 | Ogle | 604/413 |
| 3,995,630 | A | * | 12/1976 | van de Veerdonk | 604/416 |
| 4,180,070 | A | * | 12/1979 | Genese | 604/88 |
| 4,808,184 | A | * | 2/1989 | Tepic | 604/87 |
| 5,797,678 | A | * | 8/1998 | Murray | 366/139 |
| 5,934,803 | A | * | 8/1999 | Hutter | 366/139 |
| 6,024,480 | A | * | 2/2000 | Seaton et al. | 366/139 |
| 6,042,262 | A | * | 3/2000 | Hajianpour | 366/139 |
| 6,116,773 | A | * | 9/2000 | Murray | 366/139 |
| 6,176,607 | B1 | * | 1/2001 | Hajianpour | 366/139 |
| 6,210,031 | B1 | * | 4/2001 | Murray | 366/139 |
| 6,312,149 | B1 | * | 11/2001 | Sjovall et al. | 366/130 |
| 6,379,033 | B1 | * | 4/2002 | Murray | 366/139 |

* cited by examiner

Primary Examiner—Tony G. Soohoo
(74) Attorney, Agent, or Firm—Lowenstein Sandler PC

(57) ABSTRACT

By providing a fluid transfer assembly, two components forming bone cement are maintained separately from each other until actual intermixing thereof for use is desired, with the liquid monomer component being completely dispensed from a sealed unit directly into the mixing vessel in a closed loop manner, without exposure thereof to the user and without breakage of the container holding the liquid monomer, and a unique, multi-component, product handling and delivering system is achieved. In accordance with the present invention, the fluid transfer assembly is constructed for cooperating with the sealed vial or tube containing the liquid monomer and the mixing vessel for completely extracting all of the liquid monomer from the vial/tube in a closed loop operation and directly delivering the liquid monomer into the mixing vessel containing the dry powder. This transfer operation is achieved upon demand by the user, while preventing the liquid monomer from being exposed to the user or to the surrounding area.

17 Claims, 5 Drawing Sheets

MULTI-COMPONENT, PRODUCT HANDLING AND DELIVERING SYSTEM

RELATED APPLICATIONS

This application is related to U.S. Provisional Patent Application Serial No. 60/327,655, filed Oct. 9, 2001 entitled MULTI-COMPONENT, PRODUCT HANDLING AND DELIVERY SYSTEM.

TECHNICAL FIELD

This invention relates to a multi-component transfer system for enabling at least two components to be positioned in a mixing chamber for subsequent processing.

BACKGROUND ART

In many surgical procedures, particularly orthopedic procedures, it has now become common to affix a prosthesis to a bone or joint structure for improving the strength, rigidity, and movement of the bone/joint structure. Although such prosthetic devices have been widely used, hip joints and knee joints are the most common examples of areas where prosthetic devices are used to reduce or eliminate pain and suffering that exists from typical leg movements.

As part of these operations, it has become common practice to secure the prosthesis to the bone or joint using a cement, formed by intermixing a powder and a liquid. Once intermixed, the two components must be thoroughly blended together to achieve the required consistency for the fully mixed cement, with the fully mixed cement then being loaded into a dispensing apparatus for placement in the desired area for affixing the prosthesis to the desired site.

In most applications, the two components forming the cement are mixed in a mixing vessel and, once fully mixed, are manually transferred from the mixing vessel to a dispensing member. Typically, devices such as caulking guns are employed, for dispensing the fully mixed cement to the precisely desired location of the patient. This process is extremely unpleasant for individuals mixing the cement, since the mixed cement contains an offensive, noxious odor. Furthermore, removal of the mixed cement from the mixing vessel into the caulking gun is cumbersome, time consuming, and has the potential for being mishandled and/or dropped.

Another problem typically encountered with prior art systems is the difficulty encountered with air being entrapped in the mixed cement. The presence of air pockets or air bubbles in the mixed cement is undesirable. Since it is important that the cement added to the bone area for affixing the prosthetic be virtually free of any entrapped air bubbles or air pockets, most prior art systems demand mixing of the powder and liquid under vacuum conditions. As a result, added limitations are incurred on the flexibility of the mixing vessel and the ability to mix the two-part cement mixture in any desired location.

Some prior art systems have enabled the mixing to be performed in one vessel which then is directly connected to a feeding system for enabling the mixed cement to be added to a holding tube for use with the dispensing caulking gun. However, a separate dispensing system is required and extra handling and exposure of the mixed cement to the surrounding personnel is required. Furthermore, care must be exercised during the transfer of the mixed cement to the dispenser, since air is frequently introduced into the cement during this transfer operation as well as the risk of dropping or spilling the material.

More recently, a unitary, fully integrated, bone cement mixing and dispensing system has been attained. This unique achievement is realized by creating a single housing or member which comprises a mixing chamber integrally combined with a delivery chamber or tube. The delivery chamber terminates with a portal through which the mixed bone cement is directly dispensed to any desired location.

In order to provide a mixing chamber which can be operated independently of the delivery chamber, the two chambers of the integrated system are movable between two alternate positions. In the first position, each chamber is sealed from the other, while in the second position, the two chambers are in direct communication with each other.

By employing this new development, the two components forming the bone cement are placed in the mixing chamber and intermixed, with complete assurance that no unmixed bone cement will enter the delivery chamber. Complete mixing of the bone cement is assured by providing, in some embodiments, an integrated counter and display which informs the operator the exact time at which the cement components have been thoroughly intermixed.

Once the two components forming the bone cement are fully intermixed with each other, to provide the desired bone cement product, the integrated, dual chamber system of the present invention is moved from its first sealed position to its second open position, enabling the fully mixed bone cement to be transferred from the mixing chamber directly into the delivery chamber. When desired and under the complete control of the operator, the mixed bone cement is advanced through the delivery chamber to a delivery portal, formed at the terminating end thereof. Then, the fully intermixed bone cement is dispensed through the portal directly to the desired location where the product is to be used.

Although this prior art integrated bone cement mixing and delivery system has been successful in overcoming many prior art problems, one problem that has continued to plague this industry is the difficulty encountered in the delivery, shipment, and transfer of the two components which form the bone cement. As is well-known, bone cement comprises a first component which consists of a dry powder and a second component which consists of a liquid monomer.

These components must be kept separate from each other until the user is ready to intermix the components to form the desired bone cement. Typically, the dry powder is stored in a flexible bag, pouch, or similar container, while the liquid monomer is stored for shipment and handling in a vial or tube, usually formed from glass.

In use, the container holding the dry powder which forms a first component is opened and the powder is placed in the mixing vessel. Then, when creation of the cement is desired, the glass vial or tube holding the liquid monomer is opened and the monomer is added to the powder. Thereafter, the two components are thoroughly intermixed with each other.

In attempting to expedite the opening of the vial or tube holding the liquid monomer, as well as reduce any exposure to the foul odor possessed by the liquid monomer, various prior art systems have been developed for enabling the user to insert the sealed vial or tube into an area of the mixing vessel and then break the vial or tube for releasing the liquid monomer directly into the dry powder.

These prior art systems all require that the broken glass pieces or shards of the vial/tube must be separately retained and prevented from reaching the cement product. In attempting to satisfy this requirement, substantial construction and operational difficulties have occurred with these prior art systems. Furthermore, in other prior art systems, manual addition of the monomer is required, exposing the user to the foul odor of the monomer and the substantial difficulties typically encountered in handling such products.

Therefore, it is a principal object of the present invention to provide a multi-component, product handling and delivering system which controllably enables the liquid monomer to be automatically delivered to the dry powder when desired.

Another object of the present invention is to provide a multi-component, product handling and delivering system having the characteristic features described above which comprises a fully integrated structure which eliminates the requirement for independent transfer of the components which form the mixed cement and eliminates the breakage of any vial or tube.

Another object of the present invention is to provide a multi-component, product handling and delivering system having the characteristic features described above which is easy to use and is virtually fool-proof in its operation.

Another object of the present invention is to provide a multi-component, product handling and delivering system having the characteristic features described above which provides intermixed bone cement virtually devoid of entrapped air pockets or air bubbles.

Another object of the present invention is to provide a multi-component, product handling and delivering system having the characteristic features described above which is easily employed by any individual, free from unwanted odors and product handling difficulties.

Other and more specific objects will in part be obvious and will in part appear hereinafter.

SUMMARY OF THE INVENTION

By employing the present invention, all of the prior art difficulties and drawbacks have been overcome and a unique, multi-component, product handling and delivering system is achieved. In the present invention, the two components forming the bone cement are maintained separately from each other until actual intermixing thereof for use is desired, with the liquid monomer being completely dispensed from a sealed unit directly into the mixing vessel in a closed loop manner, without exposure thereof to the user and without breakage of the container holding the liquid monomer.

Throughout the following disclosure of the present invention, the multi-component, product handling and delivery system is detailed as a component of an integrated bone cement mixing and delivery system. Due to the unique attributes and substantial advances that have been achieved by the integrated bone cement mixing and delivery system, the present invention is preferably employed in combination with an integrated bone cement mixing and delivery system. However, the present invention is equally applicable to all mixing vessels for bone cement which may be employed with equal efficacy. Consequently, although specific reference to the integrated bone cement mixing and delivery system is found throughout this disclosure, the invention defined herein can be used with any mixing vessel without departing from the scope of this invention.

In accordance with the present invention, the multi-component, product handling and delivering system comprises a mixing vessel within which the dry powder forming the first component of the bone cement is preferably stored, directly in the mixing vessel for shipment therewith. Alternatively, if desired, the powder material may be contained in a sealed bag, pouch, container, or the like which is opened to dispense the powder directly into the mixing vessel. However, in the preferred embodiment, the powder is stored directly in the mixing vessel ready for use.

In addition, the multi-component, product handling and delivering system comprises a sealed vial or tube on which a cap or closure is mounted, with the second component of the bone cement, namely the liquid monomer, stored therein. In the preferred construction, the cap or closure incorporates a zone or integrally formed area which comprises an elastomeric material, such as elastomeric plastics, rubbers, silicones, and the like.

Caps or closures of this nature are well known in the medical field, with the zone being commonly referred to as a "septa". Typically, such caps or closures are found on vials or containers incorporating liquid medicines which are dispensed through hypodermic needles or syringes. By piercing the septa with the hypodermic needle or syringe, entry into the vial is attained, without loss of any medicine through the cap or closure. This is due to the ability of the septa to seal about the needle when inserted. In addition, once the syringe has been filled and the needle withdrawn, the septa completely closes the aperture formed by the needle, preventing any leakage of medicine therethrough.

In the present invention, the liquid monomer is contained in a vial or tube which incorporates a cap or closure having a septa-like construction. In this embodiment, the septa-bearing vial or tube completely seals the liquid monomer in the vial while enabling a needle or similar piercing element to enter the septa to gain access to the liquid monomer, without any loss of liquid monomer through the aperture that has been formed.

In order to attain the desired transfer of the liquid monomer from the sealed vial or tube directly into the dry powder, without exposing the user to the liquid monomer, the multi-component product handling and delivering system of the present invention comprises a fluid transfer assembly. The fluid transfer assembly of this invention is constructed for cooperating with the sealed vial or tube containing the liquid monomer and the mixing vessel for completely extracting all of the liquid monomer from the vial/tube in a closed loop operation and directly delivering the liquid monomer into the mixing vessel containing the dry powder. This transfer operation is achieved upon demand by the user, while preventing the liquid monomer from being exposed to the user or to the surrounding area.

In its preferred construction, the present invention, the fluid transfer assembly comprises a housing incorporating two portal bearing mounting collars formed thereon and two cooperating, hollow, piercing elements integrally affixed therewith. In the preferred construction, the two cooperating hollow piercing elements comprise hypodermic needle-like constructions which are coaxially associated with each other to provide a substantially continuous elongated flow path therethrough.

In addition, each piercing element comprises a sharp tip portion constructed for piercing through septa-like materials associated with the mixing vessel and the monomer bearing vial or tube. Furthermore, one piercing element is associated with one mounting collar of the liquid transfer assembly.

In addition, the mixing vessel of the present invention incorporates a first portal for cooperating with one of the mounting collars of the fluid transfer assembly and a second portal constructed for being interconnected to a vacuum source. By employing these elements, a completely closed loop, substantially sealed, delivery of the liquid monomer directly into the dry powder for forming the bone cement in the mixing vessel is attained.

In the preferred construction, the first portal of the mixing vessel, which is constructed for being interengaged with a mounting collar of the fluid transfer assembly, incorporates a small disk formed of elastomeric material mounted therein. By employing elastomeric material such as elastomeric plastics, rubbers, silicones, and the like, the interior of the mixing vessel is maintained completely sealed, accessible only by the insertion of a needle-like device through the disk.

In operation, whenever a user is ready to form the bone cement for use in a particular application, the dry powder is placed in the mixing vessel, unless the dry powder has previously been mounted therein. Then, the liquid monomer containing vial/tube is selected and the first collar of the housing of the fluid transfer assembly is telescopically mounted directly onto the septa-bearing cap or closure of the vial/tube. This telescopic mounting procedure causes the syringe-like piercing element associated therewith to be inserted through the septa, thereby gaining access to the interior of the vial/tube.

Thereafter, the second collar of the housing of the fluid transfer assembly is mounted directly on the collar-receiving portal of the mixing vessel. This mounting procedure causes the second piercing element of the fluid transfer assembly to be inserted through the sealing disk mounted in the portal of the mixing vessel. In this way, direct communication between the interior of the vial/tube and the mixing vessel is established, in a completely closed loop, sealed construction.

Once all of the components are mounted in place, the vacuum connected to the second portal of the mixing vessel is activated causing the liquid monomer to be drawn through the piercing elements of the fluid transfer assembly, causing the liquid monomer to be fed directly onto the dry powder contained in the mixing vessel. Once all of the liquid monomer has been transferred into the mixing vessel, the empty vial/tube is removed, along with the fluid transfer assembly, and mixing of the two components is initiated.

As is evident from the foregoing discussion, the removal of the fluid transfer assembly from the first portal of the mixing vessel causes of the sealing disk mounted therein to be immediately closed, as soon as the piercing element is removed therefrom. As a result, the interior chamber of the mixing vessel is continuously sealed from the surrounding environment, preventing any unwanted foul odors to emanate from the mixing vessel.

The invention accordingly comprises the features of construction, combination of elements and arrangement of parts which will be exemplified in the construction hereinafter set forth, and the scope of the invention will be indicated in the claims.

THE DRAWINGS

For a fuller understanding of the nature and objects of the invention, reference should be had to the following detailed description taken in connection with the accompanying drawings, in which.

DETAILED DISCLOSURE

Figure 1:
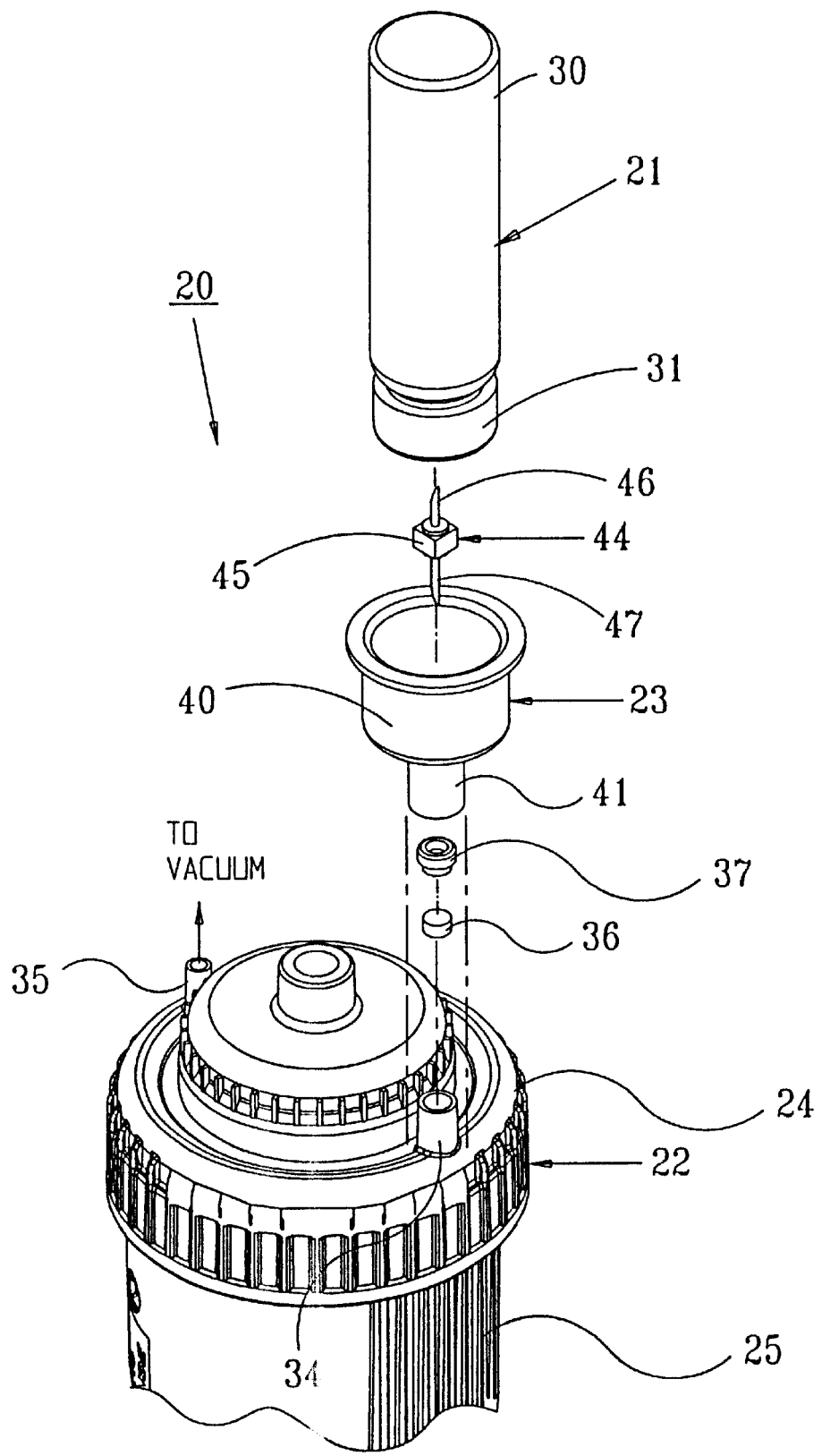
FIG. 1 is an exploded perspective view, partially broken away, depicting the multi-component product handling and delivering system of the present invention.

By referring to FIGS. 1–11, along with the following detailed discussion, the construction and operation of the preferred multi-component product handling and delivering systems of the present invention can best be understood. However, as will become evident from this disclosure, further alternate embodiments of the present invention can be implemented without departing from the scope of the present invention. Consequently, the embodiments detailed in FIGS. 1–11, and in the following detailed disclosure, are intended for exemplary purposes, and not as a limitation of the present invention.

In addition, as mentioned above, the present invention may be employed with any type of mixing vessel used to intermix the two components forming the bone cement. However, due to the unique attributes provided by the integrated, bone cement mixing and delivering system, as fully detailed in U.S. Pat. Nos. 5,876,116; 5,961,211; and 6,033,105, the present invention is discussed in combination with an integrated bone cement mixing and delivery system. However, it is to be understood that the use of the present invention is not limited thereto, and the multi-component product handling and delivering system of the present invention can be employed with equal efficacy with any desired bone cement mixing system.

In FIGS. 1, 2, 6, and 7, multi-component product handling and delivering system 20 of the present invention is fully depicted as comprising liquid monomer bearing container 21, integrated bone cement mixing and delivery system 22, and fluid transfer assembly 23. As shown, integrated bone cement mixing and delivery system 22 comprises cover 24 which is threadedly mounting to mixing vessel 25.

Figure 2:
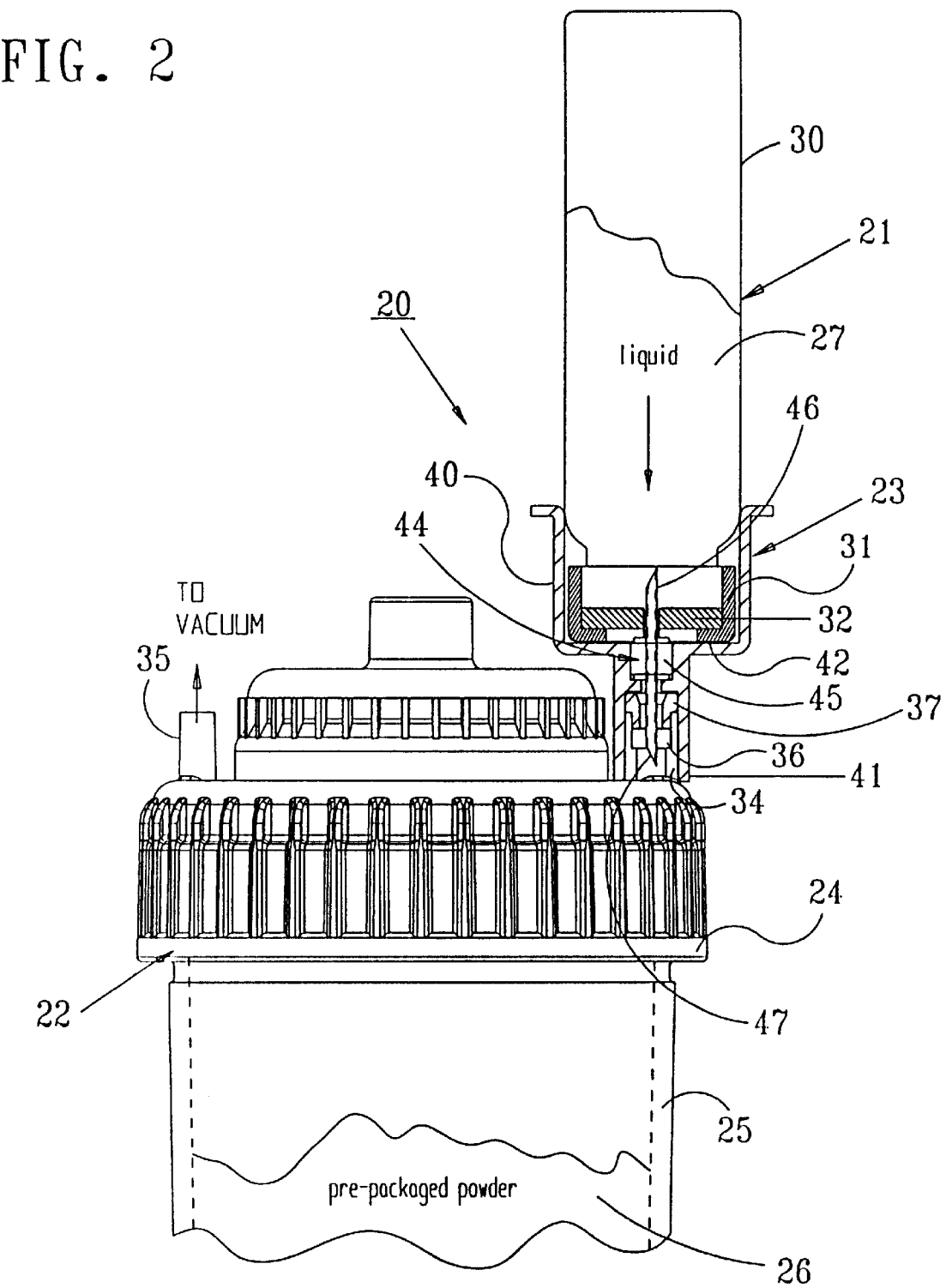
FIG. 2 is a side elevation view, partially broken away and partially in cross-section depicting the multi-component product handling and delivering system of FIG. 1 fully assembled.
Figure 3:
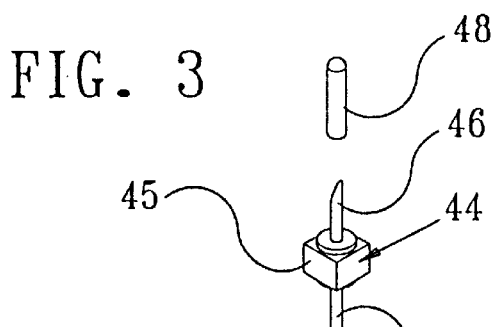
FIG. 3 is an exploded perspective view of the fluid transfer assembly member of the multi-component product handling and delivering system of present invention.
Figure 4:
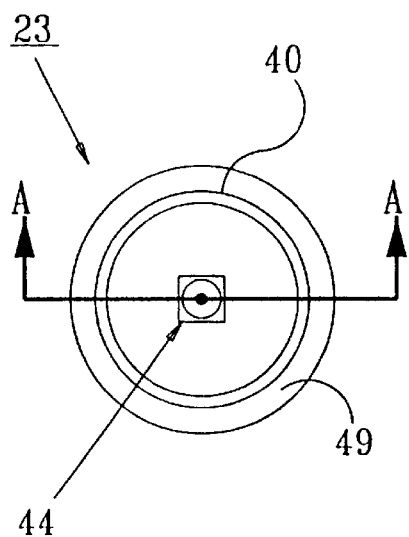
FIG. 4 is a top plan view of the fluid transfer assembly of FIG. 3.
Figure 5:
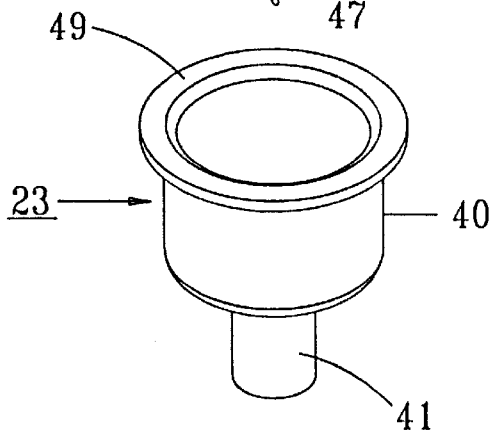
FIG. 5 is a cross-sectional side elevation view of the fluid transfer assembly taken along the line 5—5 of FIG. 4.
Figure 5:
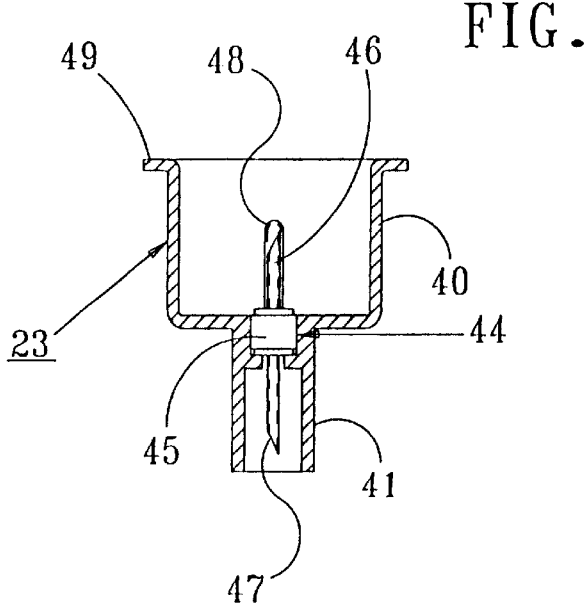
Figures 6, 7:
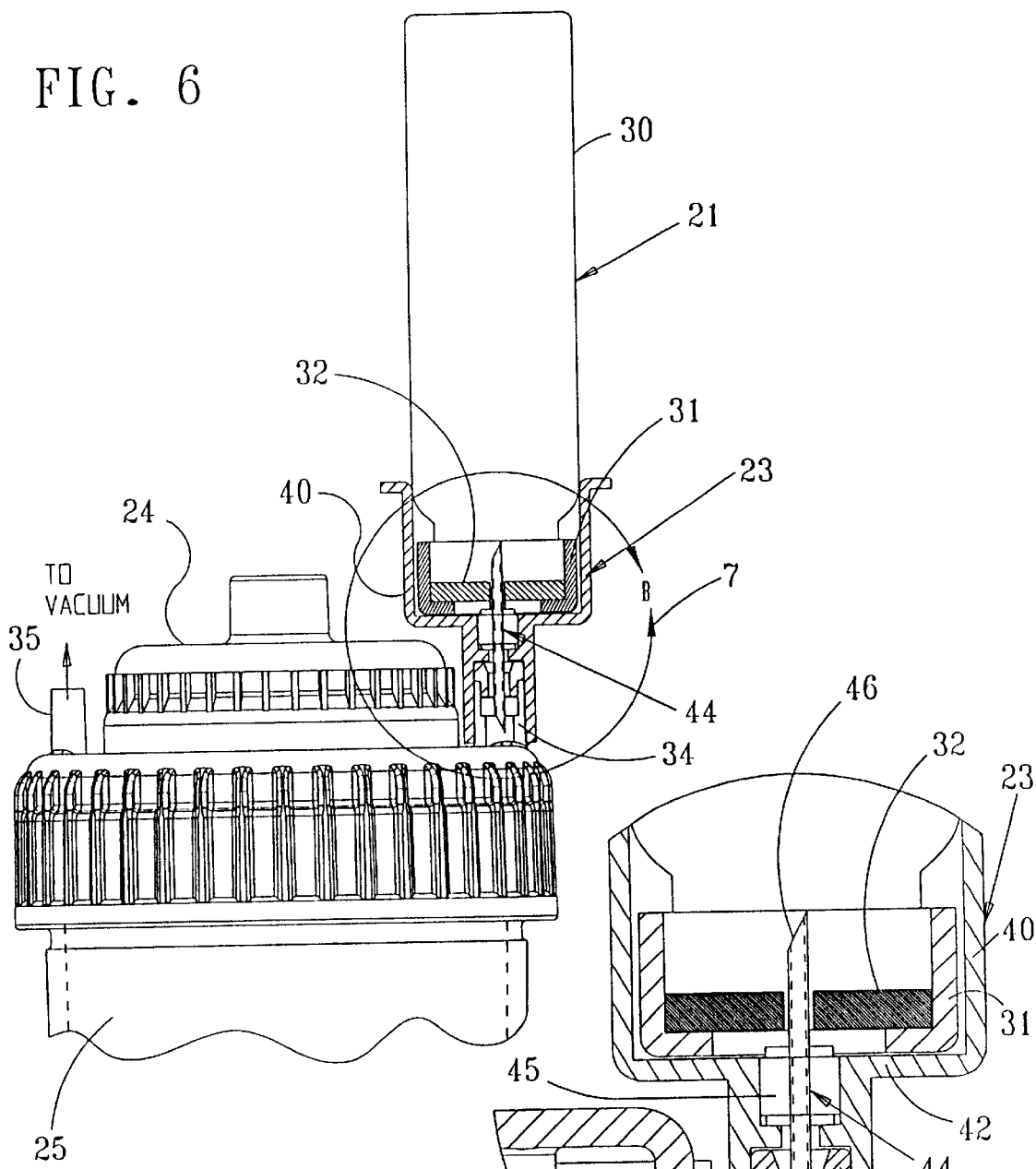
FIG. 6 is a side elevation view of the fully assembled multi-component system of the present invention, partially broken away and partially in cross-section.
FIG. 7 is an enlarged cross-sectional side elevation view detailing area 7 of FIG. 6.

In the preferred construction and implementation of the present invention, the first component of the bone cement, which comprises dry powder 26, is stored in mixing vessel 25 of bone cement mixing and delivery system 22, as clearly shown in FIG. 2. However, if desired, dry powder 26 may be stored in any suitable container, bag, or pouch which is opened just prior to use with the powder being added to mixing vessel 25.

In addition to preferably shipping dry powder 26 in mixing vessel 25 of bone cement mixing and delivery system 22, the second component, which comprises liquid monomer 27, is contained in container 21. In its preferred construction, container 21 comprises glass vial or tube 30 having a single opening or portal on which cap or closure 31 is mounted.

As detailed above, cap or closure 31 of container 21 comprises an integrally formed septa to provide access to the interior of glass vial/tube 30. Septa 32 comprises a generally conventional construction, formed of elastomeric material, which typically comprises elastomeric plastics, rubbers, silicones, and the like. In this way, liquid monomer 27 is completely sealed within glass tube/vial 30, while providing access to the interior of tube/vial 30 only by the use of a suitable needle or syringe.

In addition, cover 24 of bone cement mixing and delivery system 22 comprises portals 34 and 35 which are mounted thereto and provide access to the interior of mixing vessel 24. Portal 35 comprises a generally conventional construction which enables a vacuum source to be connected thereto, using any suitable conduit or tube. In addition, portal 34 comprises a septa-like disk 36 mounted in portal 34 for sealing the interior of mixing vessel 25 from the ambient air, while also enabling access to the interior of mixing vessel 25 to be achieved by employing a suitable needle or syringe.

Finally, holder 37 is employed for maintaining septa-like disk 36 in the precisely desired position within portal 34. By forming holder 37 with two separate and distinct diameters, one portion of holder 37 is inserted into portal 34, while the second, larger diameter portion thereof engages the outer terminating edge of portal 34. In this way, sealing disk 36 is securely maintained in the desired position within portal 34.

The construction of fluid transfer assembly 23 of the present invention is completed by providing for mating engagement thereof with cap 31 of container 21 and portal 34 of cover 24 of mixing and delivery system 22. As fully depicted in FIGS. 1–7, in its preferred embodiment, fluid transfer assembly 23 comprises collar portions 40 and 41, interconnected with each other along support plate 42. In addition, collar portions 40 and 41 preferably comprise generally cylindrical shapes and are coaxially aligned with each other.

In addition, collar portion 40 is constructed with an inside diameter dimensioned for co-operative, frictional engagement with cap 31 of container 21. In this way, when fluid transfer assembly 23 is mounted to container 21, fluid transfer assembly 23 is frictionally engaged securely with container 21, preventing any unwanted, easy dislodgment of container 21 from assembly 23.

Similarly, collar 41 comprises an inside dimension constructed for mating, co-operative, sliding engagement with portal 34 of cover 24. In addition, by designing collar 41 with an inside dimension which is slightly greater than the outside dimension of portal 34, secure holding engagement of fluid transfer assembly 23 with portal 34 is achieved whenever assembly 23 is telescopically mounted into overlying engagement with portal 34.

In order to complete the construction of fluid transfer assembly 23, dual ended piercing element 44 is employed. As depicted, dual ended piercing element 44 comprises a support base 45, a needle forming member 46 mounted to one surface of support base 45 and a needle forming member 47 mounted to the opposed surface of support base 45.

In the preferred construction, needle forming members 46 and 47 comprise elongated, hollow tubes mounted to support base 45 in coaxial alignment with each other, forming a continuous, elongated flowpath therebetween. In addition, each needle forming member 46 and 47 comprises sharp, pointed, distal ends constructed for piercing any septa-like material for gaining access to the interior associated with the septa-like material seal member.

In addition, base 45 of piercing element 44 is securely mounted in fluid transfer assembly 23, preferably affixed in support plate 42. When mounted in its secure position, needle forming member 46 extends into collar portion 40, substantially centrally disposed therein. In this position, needle forming member 46 is peripherally surrounded by the wall forming collar portion 40 with its sharp, distal end extending toward the open portal or collar 40.

Similarly, needle forming member 47 is securely positioned to be centrally disposed within collar portion 40, peripherally surrounded by the wall forming collar 41. In addition, the sharp distal end of needle forming portion 47 extends towards the open portal of collar 41.

By employing this construction, the telescopic axial advance of fluid transfer assembly 23 into engagement with container 21 and portal 34 of cover 24, causes needle forming portions 46 and 47 to pierce the septa and establish a direct fluid transfer flow path between container 21 and mixing vessel 25. In the preferred construction, in order to eliminate any unwanted injuries, tip cover 48 is preferably mounted to needle forming member 46. Since the diameter of collar portion 40 is large enough to enable a finger tip to enter its portal, the use of cover 48 prior to engagement of cover 40 onto cap 31 provides the desired protection.

In addition, in the preferred construction, collar 40 comprises radially extending flange 49 formed on its terminating end. By employing flange 49, ease of use and control of collar 40 is provided.

By referring to FIGS. 8–11, along with the following detailed discussion, the construction of an alternate, preferred embodiment of fluid transfer assembly 23 of the present invention is provided. In this embodiment, fluid transfer assembly 23 comprises a housing 54 which incorporates collar portions 55 and 56, interconnected to each other by support wall 57. In the preferred embodiment, collar portions 55 and 56 preferably comprise generally cylindrical shapes and are vertically aligned with each other. In addition, the central axis of each collar portion is parallel to each other and offset from each other.

As with the embodiment detailed above, collar portion 56 comprises an inside diameter constructed for mating, co-operative, sliding engagement with portal 34 of cover 24. In addition, by designing collar portion 56 with an inside diameter which is slightly greater than the outside diameter of portal 35, secure holding engagement of fluid transfer assembly 23 with portal 34 is achieved whenever assembly 23 is telescopically mounted into overlying engagement with portal 34.

In addition, collar portion 55 comprises an inside diameter dimensioned for co-operative, frictional engagement with cap 31 of container 21. In addition, in this embodiment, collar portion 55 comprises a plurality of tabs 58 mounted to the inside wall of collar portion 55 which extend radially inwardly therefrom. In addition, tabs 58 are formed on the inside wall of collar portion 55 in a vertical position which is slightly greater than the vertical height of cap 31 of container 21. Finally, in the preferred construction, tabs 58 are formed about the inside wall of collar portion 55 substantially equidistant from each other, thereby being spaced apart a distance of about 120°.

By employing this construction, whenever container 21 is telescopically inserted into collar portion 55 of fluid transfer assembly 23, cap 31 of container 21 is frictionally engaged with collar portion 55, securely locked in position by tabs 58 engaging the edge of cap 31 and preventing telescopic removal of container 21 from collar portion 55. In this way, once container 21 has been mounted in secure, locked engagement with fluid transfer assembly 23, dislodgment or removal of container 21 from collar 55 is prevented.

Figure 8:
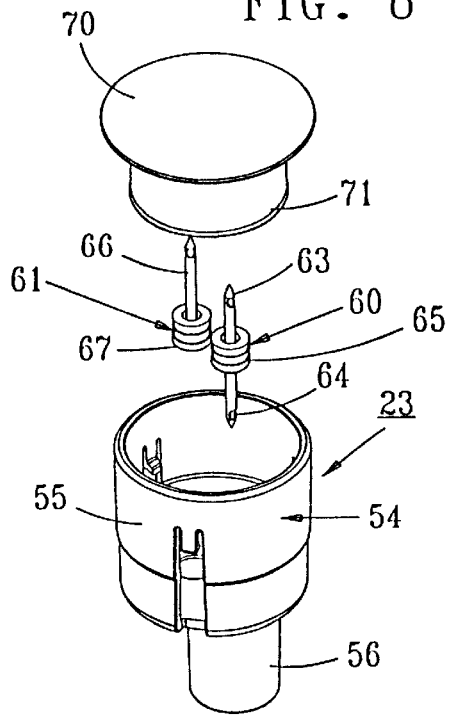
FIG. 8 is an exploded perspective view of an alternate embodiment of the fluid transfer assembly of the present invention.
Figure 9:
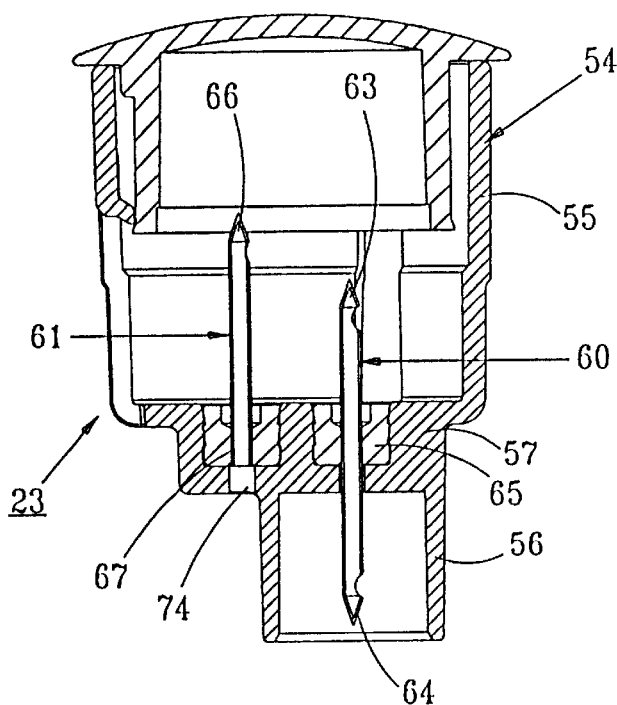
FIG. 9 is a cross-sectional side elevation view of the fluid transfer assembly of FIG. 8.
Figure 10:
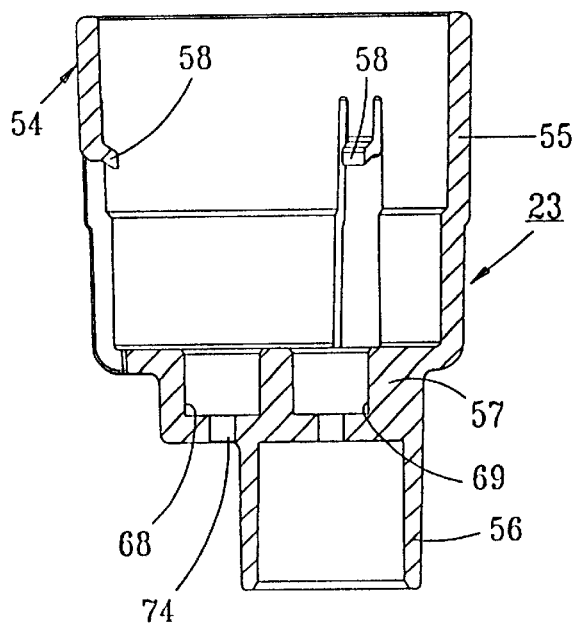
FIG. 10 is a cross-sectional side elevation view of the housing forming the fluid transfer assembly of FIG. 8.
Figure 11:
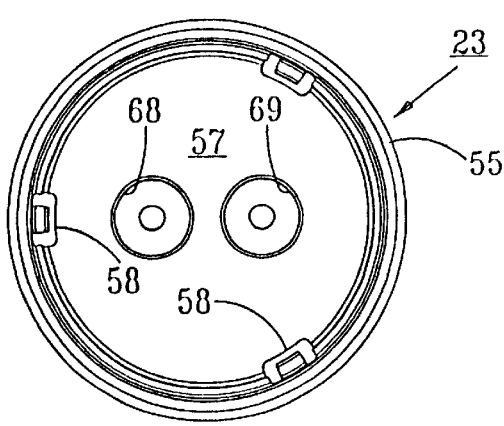
FIG. 11 is a top plan view of the housing if FIG. 10.

Furthermore, in this embodiment of the present invention, fluid transfer assembly 23 comprises two separate and independent needles or piercing elements 60 and 61 mounted in support wall 57. As shown in FIGS. 8 and 9, needle/piercing element 60 comprises an elongated, continuous, tubular member which defines an elongated flow path and incorporates two separate and independent piercing ends 63 and 64 mounted to support base 65.

With support base 65 of needle/piercing element 60 mounted in receiving hole 69 of support wall 57 of fluid transfer assembly 23, piercing end 63 extends from support wall 57 into the interior of collar portion 55, while piercing end 64 extends from support wall 57 into collar portion 56. In this way, as detailed above, whenever fluid transfer assembly 23 is mounted to portal 34 of mixing vessel 25, and container 21 is mounted to fluid transfer assembly 23, the monomer contained in container 21 is able to be transferred through needle/piercing element 60 into mixing vessel 25.

In this embodiment of the present invention, fluid transfer assembly 23 also comprises a second needle/piercing element 61 which incorporates an elongated, cylindrically shaped, hollow piercing element 66 mounted to support base 67. In the preferred construction, support base 67 is mounted in receiving hole 68 formed in support wall 57 of fluid transfer assembly 23, with hollow piercing element 66 extending therefrom into the interior of collar portion 55. In addition, base 67 of needle/piercing element 61 cooperates with aperture 74 formed in support wall 57, thereby providing an air flow path from the ambient surroundings through hollow needle/piercing element 61 into the interior of container 21 whenever container 21 is mounted in collar 55.

By employing this embodiment of the present invention, fluid transfer assembly 23 provides assurance that the monomer stored in container 21 is capable of flowing freely through needle/piercing element 60 into mixing vessel 25 whenever the monomer is desired for being added into mixing vessel 25. By providing a separate air flow pathway through aperture 74 and needle/piercing element 61, air is constantly replaced in container 21 as the monomer is withdrawn therefrom. In this way, the creation of a partial vacuum is avoided and free flow of the monomer is provided.

In the preferred construction, this embodiment of the present invention is completed by incorporating cover 70 which is constructed for being mounted in collar portion 55 for preventing and blocking any unwanted entry into collar portion 55, prior to the insertion of container 21. In this way, contact with the terminating ends of piercing elements 63 and 66 is prevented and any unwanted or accidental injury is avoided.

In the preferred construction, cover 70 comprises an outwardly extending rim 71 formed on the base thereof, which cooperates with inwardly extending tabs 58, in order to secure cover 70 in the desired position. In addition, whenever monomer bearing container 21 is ready for insertion in collar portion 55, cover 70 is easily removed from its secured position, thereby enabling container 21 to be telescopically inserted and locked in position in collar portion 55.

It will thus be seen that the objects set forth above, among those made apparent from the preceding description, are efficiently attained and, since certain changes may be made in the above article without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Having described our invention, what we claim as new and desire to secure by Letters Patent is:

1. A multi-component, product handling system constructed for enabling a first liquid component to be combined with at least one second component for being intermixed therewith, said product handling system comprising:

A. a mixing vessel constructed for receiving the first and second components and enabling the thorough mixing thereof;

B. a sealed container for storing and retaining said first liquid component and comprising a first sealing membrane for enabling the removal of said liquid component from said container through said first sealing membrane; and C. a fluid transfer assembly constructed for mating engagement with the mixing vessel and the sealed container and providing closed loop conduit means for transferring the first liquid component from the sealed container directly into the mixing vessel for being intermixed with the second component contained therein;

whereby a multi-component, product handling system is achieved which is capable of assuring direct transfer of a liquid component from a sealed container into a mixing vessel for being intermixed with additional components retained therein in a completely closed loop manner.

2. The multi-component, product handling system defined in claim 1, wherein the container comprises the first sealing membrane integrally formed therewith and constructed for retaining the liquid component sealed therein, while enabling removal of the liquid component through the first sealing membrane by piercing of the membrane with a needle-like transfer device.

3. The multi-component, product handling system defined in claim 2, wherein said container is further defined as being formed from glass and incorporates a single portal formed at one end, with a cap member sealingly closing the portal and incorporating the first sealing membrane therein.

4. The product handling system defined in claim 1, wherein said mixing vessel comprises a first portal constructed for mounted engagement with the transfer assembly.

5. The product handling system defined in claim 4, wherein the first portal comprises a second sealing membrane formed therein for restricting access to the mixing vessel, while enabling the receipt of a piercing transfer element for allowing transmission of the liquid component through said second sealing membrane into the mixing vessel.

6. The product handling system defined in claim 5, wherein said mixing vessel further comprises a membrane holding member mounted in said portal for positioning and retaining the second sealing membrane in the precisely desired location.

7. The product handling system defined in claim 1, wherein said fluid transfer assembly is further defined as comprising a housing which incorporates:

a. a first mounting collar constructed for mating engagement with the sealed container for receiving and securely holding said sealed container therewith, b. a second mounting collar constructed for mounted engagement with the first portal of the mixing vessel, and c. first conduit means mounted in the housing and extending between the first collar and the second collar for providing a fluid flow path therebetween.

8. The product handling system defined in claim 7, wherein said fluid transfer assembly is further defined as comprising a separate component removably mountable to the mixing vessel.

9. The product handling system defined in claim 8, wherein said housing forming the fluid transfer assembly is further defined as comprising a support plate formed between the first mounting collar and the second mounting collar and said conduit means is further defined as being mounted to said support plate for supporting engagement and retention thereby.

10. The product handling system defined in claim 9, wherein said conduit means is further defined as comprising two opposed terminating ends, each formed with a sharp, piercing edge, for enabling said conduit means to be easily inserted into any desired sealing membrane.

11. The product handling system defined in claim 7, wherein said fluid transfer assembly further comprises second conduit means mounted in the housing in cooperating association with an aperture formed in the housing and extending therefrom into the interior of the first collar, providing a pathway for the free flow of air.

12. The product handling system defined in claim 7, wherein said first mounting collar is further defined as comprising a plurality of tabs formed on an inside wall thereof, with said tabs radially extending inwardly from said wall and positioned for mating, locking engagement of the sealed container.

13. The product handling system defined in claim 12, wherein said first mounting collar comprises three separate and independent radially extending tabs, each of which are positioned substantially equidistant from each other.

14. The product handling system defined in claim 12, wherein said system further comprises a removable cover constructed for co-operative engagement in the first mounting collar, and secure retained holding engagement with the radially extending tabs thereof.

15. The product handling system defined in claim 1, wherein said first liquid component comprises a liquid monomer and said second components comprises dry powder for combining with the monomer to form bone cement.

16. The product handling system defined in claim 1, wherein the first sealing membrane is further defined as comprising a septa-like construction.

17. The product handling system defined in claim 1, wherein the first sealing membrane is further defined as comprising one selected from the group consisting of elastomers, rubbers, silicones, plastics, and combinations thereof.

* * * * *